United States Patent [19]

Hoffman et al.

[11] 4,376,026
[45] Mar. 8, 1983

[54] OXYGEN CONCENTRATION MEASUREMENT AND CONTROL

[75] Inventors: Alan R. Hoffman, Aurora; Thomas J. Ryan, Broadview Heights, both of Ohio

[73] Assignee: The North American Manufacturing Company, Cleveland, Ohio

[21] Appl. No.: 174,593

[22] Filed: Aug. 1, 1980

[51] Int. Cl.³ ............................................. G01N 27/58
[52] U.S. Cl. ............................... 204/195 S; 324/65 R; 324/441; 324/442
[58] Field of Search ............. 204/195 S, 1 S; 422/98; 324/445, 224, 458, 441, 442, 65 R

[56] References Cited

U.S. PATENT DOCUMENTS

| | | | |
|---|---|---|---|
| 3,056,919 | 10/1962 | Kuipers | 324/441 |
| 3,521,159 | 7/1970 | Morrow | 324/224 |
| 3,765,841 | 10/1973 | Paulson et al. | 324/442 |
| 3,915,135 | 10/1975 | Kushida et al. | 204/195 S X |
| 4,071,817 | 7/1978 | Bahl | 204/1 T X |
| 4,138,639 | 2/1979 | Hutchins | 324/445 X |

*Primary Examiner*—G. L. Kaplan
*Attorney, Agent, or Firm*—Yount & Tarolli

[57] ABSTRACT

Method and apparatus are disclosed for measuring and controlling the concentration of oxygen in a gas. A sensor (10) is provided having a zirconium dioxide wall (12). One side of the wall is exposed to a reference gas having a known oxygen concentration while the other side is exposed to a gas having the unknown oxygen concentration. An electrical potential is developed at the sensor output, where the magnitude of the potential is dependent upon the relative oxygen concentrations on either side of the sensor wall and the temperature of the wall. The reference gas is selected such that variations in the electrical potential due to temperature changes are minimized over the expected range of temperatures to which the sensor will be subjected during the oxygen concentration measurements and over the range of oxygen concentrations which must be measured.

The sensor temperature is measured by measuring the resistance of the sensor, which varies directly with temperature. An oscillator (28) provides an AC signal which is applied to the sensor (10) such that the AC signal is superimposed on the DC sensor output and has a magnitude dependent upon the resistance and therefore the temperature of the sensor. The AC and DC components are isolated from one another by two filters (32, 34) and separately utilized as temperature and oxygen concentration indications.

6 Claims, 4 Drawing Figures

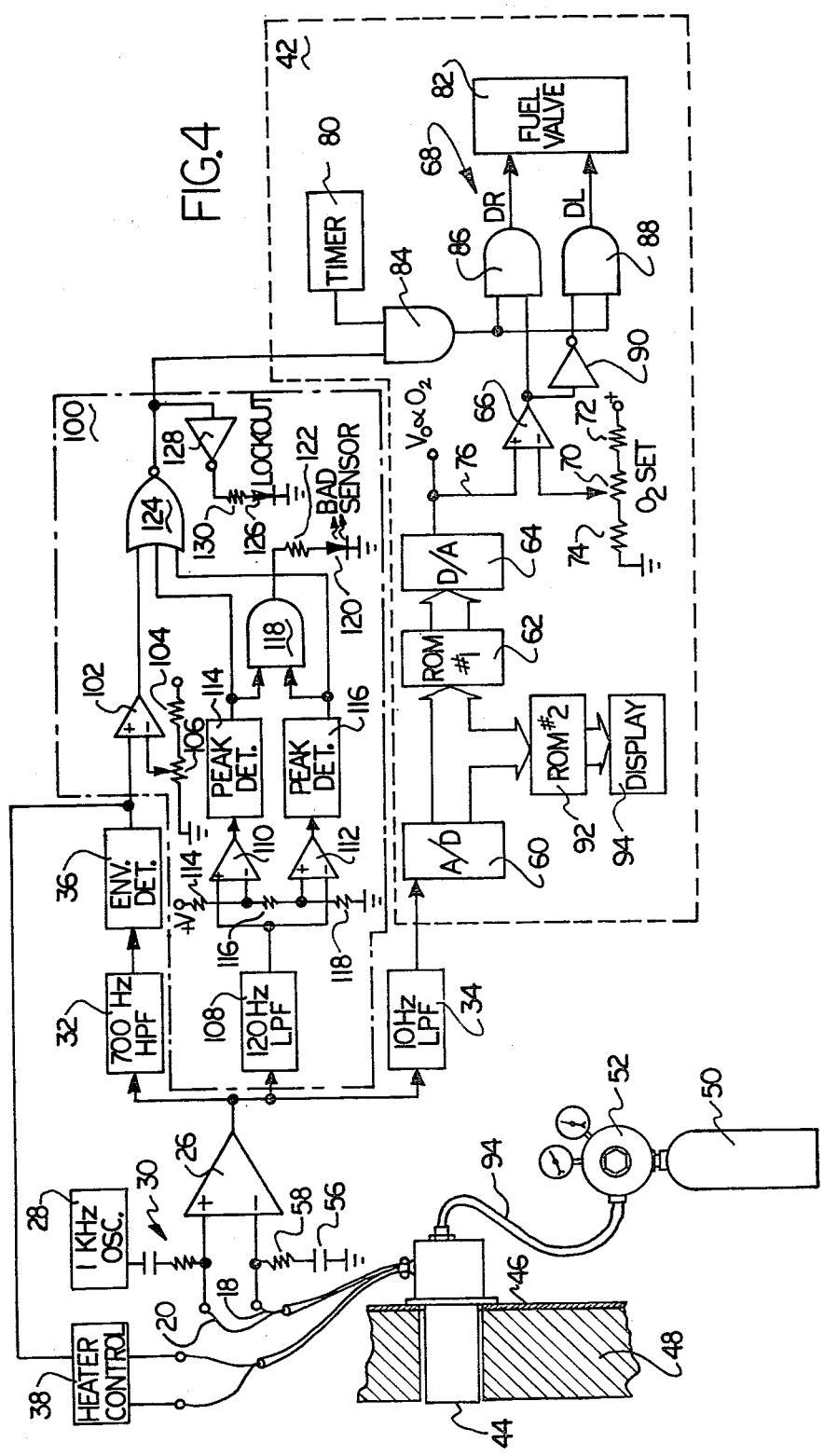

OXYGEN CONCENTRATION MEASUREMENT AND CONTROL

BACKGROUND AND FIELD OF THE INVENTION

The present invention relates to the art of oxygen concentration measurement and control and more particularly to method and apparatus for measuring and controlling the concentration of oxygen in combustion exhaust gases.

Industrial furnaces often include oxygen sensors located within the flue of the furnace for sensing the concentration of oxygen in the flue. These measurements are used to control the rate at which fuel and/or oxidizer is supplied to the furnace. Commonly, these oxygen sensors are comprised of zirconium dioxide formed into a generally test tube like shape. The closed end of the sensor is inserted within the flue of the furnace, whereas the open end is exposed to a gas having a known oxygen concentration (usually air). Electrodes were plated onto the inner and outer surfaces of the tube, and a voltage measuring device connected across these electrodes. If the oxygen concentrations on the two sides of the sensor are different, oxygen ions will diffuse through the sensor wall from the lower concentration area to the higher concentration area. The diffusion of oxygen through the sensor wall gives rise to an electrical potential across the electrodes, where the magnitude of the potential is related to the rate of oxygen flow and hence to the concentration of oxygen within the flue. This electrical potential is thus useful as an indication of the concentration of oxygen within the flue.

Unfortunately, these zirconium dioxide oxygen sensors are also sensitive to temperature changes. In other words, the magnitude of the electrical potential at the sensor output is dependent not only on the concentration of oxygen within the flue, but also upon the temperature of the sensor. Consequently, the sensor output cannot be used as a direct measure of oxygen concentration unless either the temperature of the sensor is stabilized at a known temperature or else the temperature of the sensor is taken into consideration in converting the electrical potential into an oxygen measurement. In either event it is necessary to determine the temperature of the sensor.

One prior art method of determining the temperature of the sensor is to fabricate the zirconium dioxide oxygen sensor with an integral thermocouple, whereby the thermocouple can be used to provide a direct measurement of the temperature of the sensor. Unfortunately, in such sensors it is necessary to replace the entire sensor whenever the thermocouple becomes faulted. Since ziconium dioxide oxygen sensors tend to be rather expensive (the electrodes which are plated onto the inner and outer surface of the sensor are generally platinum) this is not very desireable. Other systems have placed the thermocouple adjacent to but not integral with the sensor body itself. Patents describing sensors of this nature include the patents to Sayles, U.S. Pat. No. 3,546,086, Wilson, U.S. Pat. No. 3,720,594 and McIntyre et al., U.S. Pat. No. 3,928,161.

It is known that the resistance of the sensor changes with temperature. This characteristic has been used in the past in the determination of the temperature of the sensor. In one system an external DC electrical potential is applied to the sensor electrodes through a known resistance, with the magnitude of the resulting DC potential appearing across the sensor being used as an indication of the resistance of the sensor and, thus, the temperature thereof. Since a DC voltage is used, it is not possible to distinguish between the potential induced by the externally applied DC potential and the actual sensor output; both are DC signals. Therefore, in this system the two functions (oxygen measurement and temperature measurement) are performed sequentially rather than simultaneously. The DC output signal produced by the sensor due to the oxygen concentration within the flue is first sampled, with the amplitude of this DC signal being stored for later use. During this measurement the external DC potential is switched off so as not to perturb the output reading. Only after this is the external DC potential applied to the sensor for measurement of the sensor resistance. The DC potential then appearing across the sensor is corrected by subtracting the DC oxygen concentration signal previously measured. In this fashion, each of the two tests could be conducted without interfering with the other.

The temperature measurement derived by determining sensor resistance is then used to control the operation of a heater which maintains the temperature of the sensor within a predetermined range. Since the temperature of the sensor is still permitted to vary within this range, however, the sensor output can still be expected to vary somewhat in accordance with the temperature of the sensor. In order to avoid this, one set-point controller, known as the "Optimizer" and manufactured and sold by the assignee of this application, utilizes a reference gas having an oxygen concentration which is identical to the desired oxygen concentration in the flue. Since the output of the sensor will always be zero (regardless of temperature) when the oxygen concentration inside and outside of the sensor are the same, this simple expedient eliminates temperature variations at the set point. When the oxygen concentration in the flue differs from the desired or set point concentration, however, temperature induced deviations can still occur. This is not important in the Optimizer controller because the only point of interest is the set-point concentration; the flue oxygen concentration is never actually measured. If the output of the sensor were used for oxygen concentration measurement rather than merely set-point control, however, these temperature deviations would become troublesome.

SUMMARY OF THE INVENTION

There is described herein a method of measuring the temperature of the sensor without including a separate temperature sensor and without having to interrupt the operation of the sensor in order for the temperature measurement to take place. Also provided are method and apparatus for reducing temperature sensitivity by using a reference gas having an oxygen concentration selected such that variations in the sensor output due to temperature changes are minimized over the expected range of temperatures to which the sensor will be subjected during measurements of oxygen concentration and over the range of oxygen concentrations which must be measured.

More specifically, in accordance with the present invention an improvement is provided for use in a method of measuring the concentration of oxygen in a first gas. The method includes the steps of providing a barrier wall which develops an electrical potential across it having a magnitude which is dependent upon the relative oxygen concentrations in gases of either side of the wall and on the temperature of the wall, exposing one side of the wall to the first gas and the other side to a reference gas having a known oxygen concentration, measuring the electrical potential developed across the wall, and determining the oxygen concentration in the first gas in accordance with the results of the measurement. The improvement comprises the step of selecting a reference gas having an oxygen concentration chosen such that variations in the electrical potential due to temperature changes are minimized over the expected range of temperatures to which the wall will be subjected during the oxygen concentration measurements and over the range of oxygen concentrations which must be measured.

In accordance with another aspect of the present invention apparatus is provided for use with a sensor having an output upon which a DC output signal appears whose level is indicative of a physical parameter and whose output impedance varies with temperature. This apparatus comprises an oscillator for providing an AC signal, means for applying the AC signal to the output of the sensor so that the AC signal appears across the output of the sensor superimposed on the DC output signal and has an amplitude dependent upon the impedance of the sensor, whereby the amplitude of the AC signal appearing at the output of the sensor indicates the output impedance of, and hence the temperature of the sensor, and utilization means coupled to the output of the sensor for utilizing the level of the DC signal as an indication of the physical parameter and for utilizing the amplitude of the AC signal as an indication of the temperature of the sensor.

BRIEF DESCRIPTION OF THE DRAWINGS

The foregoing and other aspects and advantages of the present invention will become more readily apparent from the following detailed description, as taken in conjunction with the accompanying drawings, wherein:

FIG. 4 is a more detailed block diagram of an oxygen concentration measurement and control system in accordance with the teachings of the present invention.

DETAILED DESCRIPTION

In the detailed description which follows, the oxygen sensor and associated methods and apparatus will largely be described with reference to the measurement of oxygen concentration in the flue of a furnace. Of course, the invention has a wide range of uses and is suitable to most applications requiring measurement of oxygen concentration.

Figure 1:
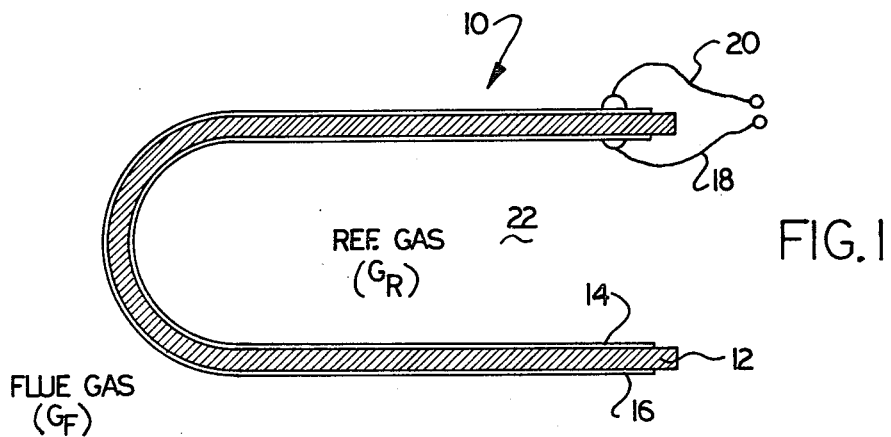
FIG. 1 is a schematic illustration of an oxygen concentration sensor of the type to which the present invention has application.

An oxygen sensor such as will find use with the method and apparatus of the present invention is generally indicated at 10 in FIG. 1 of the drawings. This sensor 10 consists of a generally test tube shaped body 12 (shown in section in FIG. 1) having an interior and exterior surface coatings 14 and 16, respectively. The generally cylindrical body 12 is formed by a zirconia dioxide material ($ZrO_2$) whereas the surface coatings 14 and 16 are formed of porous platinum. Electrical wires 18 and 20 are respectively attached to the interior and exterior surface coatings 14 and 16.

In operation, this sensor 10 will be, for example, inserted through the wall of a furnace such that the exterior of the sensor is exposed to flue gas ($G_f$) whose oxygen concentration is unknown. The interior of the sensor (generally indicated at 22) on the other hand, will be flooded with a reference gas ($G_r$) having a known oxygen concentration.

If there is a higher concentration of free oxygen molecules on the inside of the sensor than on the outside, then ions will migrate from the interior cavity 22 to the outside flue through the wall of the sensor, in the process creating a voltage difference between the inner and outer surfaces of the sensor. The rate of this ion migration is dependent upon the differences in concentration of oxygen on either side of the sensor wall, as well as upon the temperature of the sensor. The equation that describes the voltage created by this ion migration is a form of the well known "Nernst" equation, shown below:

$$E = 0.0215 \times T \times \ln \frac{(\% \ O_2 \ \text{inside})}{(\% \ O_2 \ \text{outside})} \quad (1)$$

where:
T is the sensor temperature in °K
ln is the natural logarithm function
E is the sensor output in millivolts This equation brings out that there is a logarithmic relationship between the voltage drop across the output wires 18 and 20 and the ratio of the oxygen concentrations inside and outside of the sensor. Furthermore, for a given oxygen concentration ratio the output voltage is directly dependent upon the temperature of the sensor.

Figure 2:
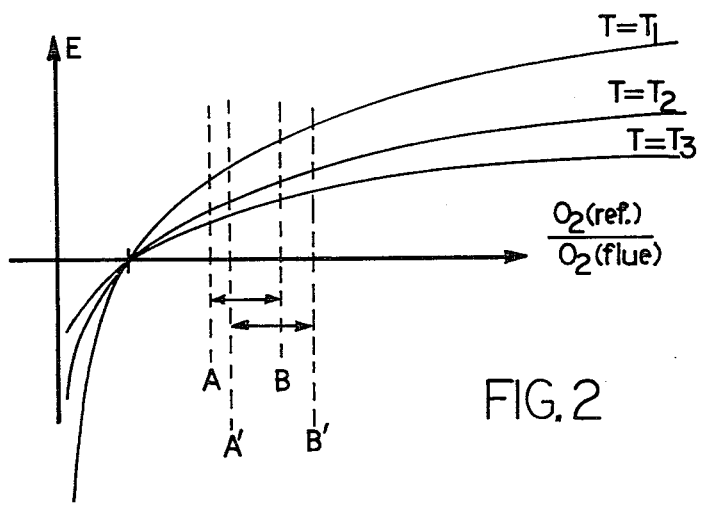
FIG. 2 is a graphical representation of the output of an oxygen sensor such as that of FIG. 1, illustrating the fashion in which the output potential varies with temperature and oxygen concentration.

This equation is shown in graphical form for three different temperatures in FIG. 2. In this Figure the dotted lines A and B represent hypothetical upper and lower limits of the oxygen concentration ratio which might be expected for a given reference gas in a given application. The actual millivoltage output from the sensor at any given oxygen concentration ratio is clearly seen to be temperature dependent. Furthermore, the magnitude of this dependence is related to the location and extent of the range A-B, which in turn is related to the oxygen concentration in the reference gas which is selected. Thus, for example, if a different reference gas is selected having a higher oxygen concentration, then the same variation in flue gas oxygen concentration might move the boundaries A and B to the primed positions A' and B' indicated in FIG. 2.

The magnitude of the error (measured in $\%O_2$ in the flue) introduced by the change in temperature at various reference oxygen concentration values is difficult to characterize and does not vary in a convenient linear manner. It is nonetheless possible, however, to select a reference gas oxygen concentration such that deviations introduced by variations in temperature over the expected flue gas oxygen range are minimized.

Thus, for example, it has been found that a reference gas oxygen concentration of 4% represents the optimum when it is desired to measure the oxygen concentration in a flue gas wherein the expected range of the measurements will be from 0.5% to 5.5% oxygen concentration and wherein the expected temperature range of the sensor varies between 1200° K and 2700° K.

This optimum is derived from the following table, which lists the maximum error in percent $O_2$ over the range of flue gas oxygen concentrations at five different temperatures. It is apparent from this table that minimum temperature-related errors occurred at 4% reference oxygen concentration. In this table, the error at 2000° K is always equal to zero since the calculations presume that the sensor is at a 2000° temperature. Unless otherwise noted, all of the maximum errors indicated in the following chart occurred at a flue gas oxygen concentration of 5.5%.

TABLE I

Max Error in % $O_2$ Resulting From Presumption That Probe Temperature is 2000° K., Over Flue Gas $O_2$ Concentration Range of .5%–5.5% $O_2$ and Temperature Range From 1200°–2700° K.

| % $O_2$ in ref. | Actual Probe Temperature (°K.) | | | | |
|---|---|---|---|---|---|
| | 1200° | 1600° | 2000° | 2400° | 2700° |
| 1% | −2.3 | −1.3 | 0 | 1.8 | 3.4 |
| 2% | −1.5 | −.8 | 0 | 1.0 | 1.8 |
| 3% | −1.0 | −.5 | 0 | .6 | 1.0 |
| 4% | .6 (1%)* | −.3 | 0 | .3 | .5 |
| 5% | .7 (1.5%)* | .3 (1.5%)* | 0 | −.3 (2%)* | −.5 (2%)* |

*parenthetical figures indicate the flue gas $O_2$ concentration at which the indicated error occurred; all other error values occurred at a 5.5% flue gas $O_2$ concentration.

To calculating these values, the millivoltage output of the sensor at a given ratio and actual temperature was calculated through use of the foregoing equation. Using the resulting millivoltage reading, a new oxygen ratio value was derived by again using the same equation, but presuming the sensor to be at temperature of 2000° K. This oxygen ratio measurement was then compared with the actual oxygen concentration measurement to derive an error figure in %$O_2$, with a maximum such %$O_2$ error figure over the selected range of flue oxygen concentrations being included in the above table.

An optimum reference gas oxygen concentration can be determined in similar fashion for any given temperature range and unknown oxygen concentration range. The resulting optimal reference $O_2$ concentration value, selected from a chart similar to that of the above Table, can then be used with the assurance that the variations introduced by temperature changes over the entire expected range of unknown oxygen concentrations will have been minimized.

It is common practice to provide a heater for controlling the temperature of the sensor so that the sensor temperature may be maintained within a preselected range. It is necessary in such applications to provide some means for determining the sensor temperature. As mentioned previously, the resistance of the sensor is directly dependent upon the temperature of the sensor, hence sensor resistance may be used to measure sensor temperature. In accordance with the present invention, a method is provided for measuring the sensor resistance at the same time that the DC potential derived from the sensor is being used to provide a measure of oxygen concentration. Apparatus for accomplishing this is illustrated in general block diagram form in FIG. 3.

For purposes of illustration, the sensor 10 has been illustrated in simplified form as comprising merely a barrier wall 12 separating the reference gas $G_r$ from the flue gas $G_f$. Conventionally, but not necessarily, the sensor will have the form illustrated generally in FIG. 1.

The oxygen concentration measurement and control system, generally indicated at 24, includes a differential amplifier 26 whose inputs are connected to the output leads 18 and 20 of the zirconia dioxide oxygen sensor 10. An oscillator 28 is also connected to the output leads 18 and 20 through an impedance circuit 30 having a known impedance. The AC signal provided at the output of the oscillator 28 will be divided between the known impedance 30 and the unknown impedance represented by the sensor 10. Since the differential amplifier 26 normally has a very high input impedance, the loading introduced by the connection of the differential amplifier 26 in parallel with the sensor 10 may be ignored.

If the impedance of the sensor 10 is substantially equal to the known impedance 10, then an AC signal having half the amplitude of the AC signal provided by oscillator 28 will appear across the output leads 18 and 20. If the impedance of the sensor 10 is slightly higher than this, then the AC signal will be of greater magnitude, whereas if the impedance of the sensor 10 is less than this, the AC signal will have a smaller amplitude. The amplitude of the AC signal appearing across the output leads 18 and 20 therefore provides a direct measure of the impedance of the sensor 10.

This AC signal will appear on the output leads 18 and 20 essentially superimposed on the DC output signal provided by the sensor 10 in response to the difference in oxygen concentrations in the flue gas and the reference gas.

The output of the differential amplifier 26 will therefore comprise a DC signal having a magnitude dependent upon the temperature of the sensor and the ratio of the oxygen concentrations on either side of the sensor 10, and an AC signal having a magnitude which is dependent upon only the resistance of the sensor 10. Two filters 32 and 34 are connected to the output of the amplifier 26 in order to isolate the AC and DC components from one another. The high-pass filter 32 rejects the DC component and passes only the AC component, whereas the low-pass filter 34 removes the AC component, passing only the DC component to its output.

An envelope detector 36 is connected to the output of the high-pass filter 32 and detects the amplitude of the AC signal isolated by the high-pass filter 32. The signal appearing at the output of the envelope detector 36 therefore has an amplitude which varies with the amplitude of the AC signal appearing across the output leads 18 and 20 of the sensor 10, and therefore also varies in accordance with the resistance of and thus the temperature of the sensor. The output of the envelope detector 36 is provided to a heater control circuit 38 which controls the application of power to heating coils 40 disposed in heat transferring relationship to the sensor 10. The heater control circuit 38 is essentially a set point controller which will control the application of power to the heating coils 10 such that the signal provided thereto by the envelope detector 36 is equal to or greater than a preset value corresponding to the desired minimum temperature of the sensor 10 (the temperature of the sensor may rise above the heater set point temperature due to heating by the furnace).

The output of low-pass filter 34, which is a DC signal having a level dependent upon temperature and oxygen concentration ratio in accordance with the above equation, is provided to an oxygen concentration controller 42. The oxygen concentration controller will control either the supply of oxygen or fuel to the combustion apparatus which is being controlled, so as to thereby indirectly control the concentration of oxygen within the flue. Also, or alternatively, this controller 42 may provide an operator readable indication of the concentration of oxygen within the flue. Errors in this oxygen concentration measurement due to temperature variations are minimized by appropriate selection of the reference gas in the previously described manner.

Figure 3:
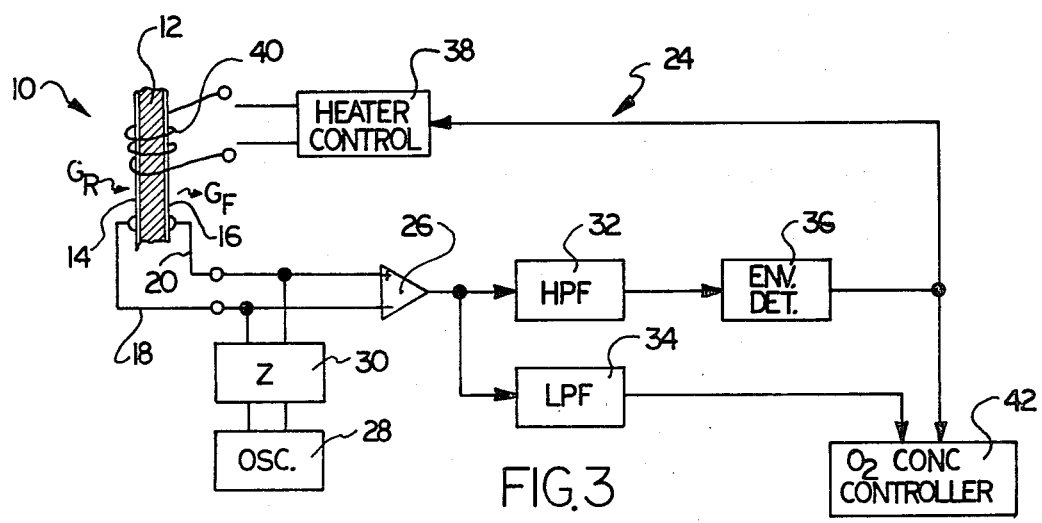
FIG. 3 is a block diagram of an oxygen concentration measurement and control system in accordance with the teachings of the present invention.

To summarize, the apparatus of FIG. 3 permits determination of the temperature of the sensor without including a separate temperature transducer and without interrupting the measurement of oxygen concentration. This is accomplished generally by producing a combined sensor output wherein the oxygen concentration measurement component and the resistance measurement component occupy separably different frequency ranges. The oxygen concentration component occurs at DC and very low frequencies, whereas the resistance measurement component occurs at a much higher frequency. The two components are then separated and independently processed.

FIG. 4 is a more detailed block diagram of an oxygen concentration measurement and control system as generally illustrated in FIG. 3. In this Figure, the sensor is shown mounted within a housing 44 which is welded, bolted, or otherwise attached to a furnace shell 46 of a refractory lined furnace (the refractory material being indicated at 48). The housing 44 will be designed to permit the free flow of flue gases around the sensor 10 contained therein. A tank 50 containing a reference gas with a preselected oxygen concentration in accordance with the criteria described previously (for purposes of example, a 4% oxygen concentration reference gas) supplies reference gas to the interior cavity of the sensor 10 contained within the housing 44. A regulator 52 regulates the flow of the reference gas into the sensor. The sensor cavity is also vented to the outside atmosphere so that there is a slow but continuous flow of fresh reference gas through the sensor.

In FIG. 4 the oscillator 28 is shown as comprising an oscillator providing an output frequency of approximately 1 kHz. This output signal is supplied to the output leads 18 and 20 of the sensor 10 through an impedance circuit 30 comprised of two similar series-connected circuits. In FIG. 4 these circuits are each comprised of a series connection of a capacitor 56 and a resistor 58. It will be noted that a circuit such as this has an impedance which varies with frequency. This impedance circuit represents a substantially higher impedance at DC and lower frequencies than it does at the 1000 kHz provided by the oscillator 28. This insures that it will not unnecessarily load the DC signal generated by the sensor.

Of course, the impedance circuit 30 might also take any number of forms other than the one illustrated in FIG. 4. In any such impedance circuit the purpose is to provide a known impedance in circuit connection to the output of the sensor such that the AC signal provided by the oscillator 28 will be divided between the known impedance and the sensor impedance.

Also in FIG. 4, the high-pass and low-pass filters 32 and 34 are shown as having break points of 700 Hz and 10 Hz, respectively. In other words, the high-pass filter 32 is designed to pass only frequencies above approximately 700 Hz, whereas the low-pass filter 34 is designed to pass only frequencies below approximately 10 Hz.

In FIG. 4, the oxygen concentration controller 42 is illustrated as comprising circuitry for providing a display of the actual concentration of oxygen within the flue and for also automatically controlling the amount of fuel supplied to the combustion apparatus in accordance with the amount of oxygen existing in the flue gases. This oxygen concentration controller 42 essentially presumes the sensor is being maintained at a temperature of approximately 2000° K. As stated previously, some variation in the actual temperature of the sensor may be expected, however due to the selection of the oxygen concentration of the reference gas contained within the tank 50, these temperature variations are minimized.

The DC signal provided at the output of low-pass filter 34 is related to the oxygen concentration within the flue, however this relationship is non-linear (specifically, logarithmic), as brought in the foregoing equation. Means are therefore provided for converting this nonlinear measure of oxygen into a linear measure. To this end, an analog-to-digital converter 60 is included which provides at its output a multibit binary digital word having a value which is linearly representative of the analog value of the DC signal provided thereto by low-pass filter 34. This digital signal therefore also non-linearly represents the concentration of oxygen within the flue. This digital signal is used to address a read only memory (ROM) 62, having a "look-up table" stored therein which relates digital sensor output values to linearized oxygen concentration values. The digital signal appearing at the output of analog-to-digital converter 60 addresses this ROM so as to access a single memory location therein storing the value which represents the linearized oxygen concentration measurement corresponding to that sensor output value. This linearized measurement appears at the output of the ROM 62 as another digital word. This digital word is then converted back into an analog value by a digital-to-analog converter 64.

The combination of analog-to-digital converter 60, read only memory 62 and digital-to-analog converter 64 functions essentially as a nonlinear amplifier whose transfer characteristics is the inverse of the nonlinear relationship between the DC potential appearing at the output of low-pass filter 34 and the actual oxygen concentration within the flue. Because of this the voltage which is provided at the output of digital-to-analog converter 64 is directly proportional to the concentration of oxygen within the flue.

This voltage signal is provided to a set point controller consisting of a comparator 66 and a drive circit generally indicated at 68. The comparator 66 compares the analog voltage appearing at the output of digital-to-analog converter 64 with an operator selectable oxygen set point derived by a resistive divider consisting of a potentiometer 70 connected in series with two resistors 72 and 74 across a positive voltage supply +V. The potential appearing at the output 76 of the digital-to-analog converter 64 is compared with the set point appearing at the wiper arm 78 of the potentiometer 70.

If the oxygen concentration is above the desired level then the potential appearing on output line 76 will be above that appearing on line 78, and the output of comparator 66 will be at a high voltage level. If, on the other hand, the oxygen concentration is below the desired value, then the signal appearing at the output 76 of digital-to-analog converter 64 will be below the potential appearing on line 78, hence the output of comparator 66 will be at a low voltage level. The output of comparator 66 therefore directly indicates whether or not the oxygen concentration is above or below the preselected level.

The output of the comparator 66 is used to gate pulses provided by a timer circuit 80 to either the drive-rich (DR) or drive-lean (DL) input to a fuel valve 82. The timer circuit 80 provides pulses on a periodic basis, for example one every two seconds. These pulses are gated to the DR and DL inputs to the fuel valve 82 through AND gate 84, 86 and 88. The AND gate 84 is a "lockout" AND gate which will block the passage of pulses from the timer circuit 80 into the AND gates 86 and 88 in the event of a sensor failure. Presuming that the sensor is operating normally, however, the AND gate 84 will be enabled so that the pulses provided by the timer circuit 80 will be applied simultaneously to an input of each of AND gates 86 and 88. The output of AND gate 86 is connected to the drive rich (DR) input to the fuel valves 82, whereas the output of AND gate 88 is connected to the drive lean (DL) input of the fuel valve 82.

The output of comparator 66 controls both AND gates 86 and 88, enabling one and only one at any given time. An input of the drive rich AND gate 86 is directly connected to the output of the comparator 66, so that AND gate 86 will be enabled whenever the output of the comparator 66 is at a high logic level. The output of the comparator 66 is connected to the AND gate 88, however, through a digital inverter 90 so that the AND gate 88 will be enabled whenever the output of the comparator 66 is at a low logic level. Thus, when the flue oxygen concentration is too high the comparator output will be high and AND gate 86 enabled to gate drive pulses to the DR input of the fuel valve. When the oxygen concentration in the flue is too low, the comparator output will be low and AND gate 88 will be enabled to gate drive pulses to the DL input of the fuel valve.

The oxygen concentration controller 42 of FIG. 4 also provides an operator readable display of the actual concentration of oxygen within the flue of the furnace. The apparatus for providing this display consists of a second read only memory 92 and a display 94. The read only memory 92 has a function similar to that of read only memory 62, except that the output of read only memory 92 is coded in binary-coded-decimal (BCD) whereas the output of read only memory 62 is coded in strict binary. This BCD output of ROM 92 is required to drive the display 94. The display 94 responds to this BCD output to provide a numerical display of the actual oxygen concentration within the flue of the furnace.

The controller illustrated in FIG. 4 includes an additional circuit 100 whose purpose is to determine whether or not the sensor is operating properly, and to disable the supply of pulses to the fuel valve in the event that it is not. Circuitry is also included for determining whether the sensor is at or above the minimum operative temperature.

A comparator circuit 102 compares the output of the envelope detector 36 (which it will be recalled, provides an output indicative of the temperature of the sensor 10) with a preset level indicating the minimum temperature within the operational temperature range of the sensor. This reference voltage is provided by a voltage divider consisting of a fixed resistor 104 and a potentiometer 106 again connected in series across a positive voltage supply +V. The output of comparator 102 will only be low if the sensor temperature is above the minimum operational temperature.

An "open sensor" condition is determined by monitoring the output of another low-pass filter 108. This low-pass filter, whose input is connected to the output of differential amplifier 26, has a break-point of 120 Hz so that the output thereof will lack the 1000 Hz resistence measurement signal but will include the 60 cycle hum which would be present on the sensor output in the event of opening of one of the leads connected to the sensor. The output of the 120 Hz break-point low-pass filter is connected to the inputs of two comparators 110 and 112 which respectively compare the input signal with reference levels corresponding with 90% and 10% of the supply voltage. As long as the output of low-pass filter 108 is between these two reference levels, both comparator outputs will be low. If the output of low-pass filter 108 is greater than 90% or less than 10% of the supply voltage, however, then the output of the corresponding comparator will shift high.

The reference levels are derived from a third potential divider consisting of three resistors 114, 116 and 118 connected in series across the positive supply of +V. Preferably, the resistors 114 and 118 will have approximately the same value, whereas the resistor 116 will have approximately ten times that value, such that the potential appearing above and below the resistor 116 correspond with approximately 90% and 10%, respectively, of the supply voltage +V.

The negative input to comparator 110 is connected to the junction between resistors 114 and 116, whereas the positive input to comparator 112 is connected to the junction between resistors 116 and 118. The output of comparator 110 will therefore be at a high voltage level in the event that the output of the low-pass filter 108 has an amplitude which is greater than 90% of the +V supply voltage, whereas the output of comparator 112 will be at a high voltage level in the event that the output of low-pass filter 108 has an amplitude which is less than 10% of the +V supply voltage. The outputs of both of the comparators 110 and 112 will be low when the signal provided at the output of low-pass filter 108 has an amplitude falling somewhere between 10% and 90% of the supply voltage.

If one of the leads to the sensor 10 opens, a significant amount of 60 cycle hum will be picked up at the inputs to the differential amplifier 26 and will be passed through the low-pass filter 108 to the comparators 110 and 112. The positive excursions of this 60 cycle signal appearing at the output of low-pass filter 108 will exceed 90% of the supply voltage, whereas the negative going excursions will drop below 10% of the supply voltage. Consequently, positive excursions will cause the output of comparator 110 to momentarily shift to a high voltage level, whereas the negative excursions will cause the output of the comparator 112 to momentarily shift to a high logic level. The outputs of both comparators 110 and 112 will therefore comprise periodic pulses occurring at a 60 cycle rate.

Peak detectors 114 and 116 detect the peak amplitude of the signals appearing at the outputs of comparators 110 and 112, respectively. These peak detectors have a time constant which is lengthy enough so that the 60 cycle signals appearing at the outputs of comparators 110 and 112 upon the occurrence of an open sensor condition will produce a substantially continuous high signal at the output of the peak detectors.

An AND gate 118 has each of its two inputs connected to a respective one of the outputs of peak detectors 114 and 116. The output of AND gate 118 will be at a low logic level unless both of the outputs of peak detectors 114 and 116 are at high logic levels, indicating an open sensor condition. A light emitting diode 120 is connected to the output of the AND gate 118 through a dropping resistor 122. This light emitting diode will become illuminated whenever the output of AND gate 118 is at a high logic level, i.e., whenever the oxygen sensor sensor has opened. Illumination of this light emitting diode therefore indicates to the operator that the sensor has failed.

As stated previously, the controller circuitry 42 illustrated in FIG. 4 incorporates an AND gate 84 for disabling the operation of the oxygen concentration controller under appropriate circumstances. The "lockout" signal used to disable the AND gate 84 is derived from a NOR gate 124 having three inputs. These three inputs are derived from the comparator 102, and peak detectors 114 and 116. The output of NOR gate 124 will shift to a low logic level in the event that a high logic level is provided to any of its three inputs. Consequently, the output of NOR gate 124 will shift to a low logic level, thereby locking out the operaton of the oxygen concentration controller, if either (1) the output of comparator 102 is at a high logic level, indicating that the sensor has not yet reached its operating temperature, (2) the output of peak detector 114 is at a high logic level, indicating that the DC signal provided at the output of the sensor is above its normal operating range, or (3) the output of peak detector 116 is at a high logic level, indicating that the DC sensor output is below its normal operating range.

A second light emitting diode 126 is connected to the output of NOR gate 124 through a logic inverter 128 and a dropping resistor 130. This light emitting diode will become illuminated whenever the output of the NOR gate 124 drops to a low logic level (thereby locking out the operation of the oxygen concentration controller 42).

Methods and apparatus have therefore been described for reducing and controlling the influence of temperature variations in oxygen concentration measurement and control system. Although the invention has been described with respect to a preferred embodiment, it will be appreciated that various rearrangements and alterations of parts may be made without departing from the spirit and scope of the present invention, as defined in the appended claims. Thus, for example, the sensor impedance measuring circuit would operate equally effectively if an AC current source were used in place of the AC voltage source and associated impedance circuit. A multiplicity of other changes are, of course, also possible and are equally within the scope of the invention.

What is claimed is:

1. Apparatus comprising:
    zirconium dioxide oxygen sensor means having an output upon which a D.C. output signal appears whose level is dependent upon temperature and the concentration of oxygen in an unknown gas relative to the concentration of oxygen in an unknown gas relative to the concentration of oxygen in a reference gas having a known oxygen concentration, and whose output impedance varies with temperature;
    means for providing and applying an AC signal to said output of said oxygen sensor means so that said AC signal appears on said output superimposed on said DC signal and has an amplitude dependent upon the impedance of said oxygen sensor means;
    means responsive to said superimposed signals for providing a first indication which is indicative of the amplitude of said AC signal and thus the temperature of said oxygen sensor means;
    means responsive to said first indication for controlling the temperature of said oxygen sensor means;
    means responsive to said superimposed signals for providing a second indication which is indicative of the amplitude of said DC signal and thus the concentration of oxygen in said unknown gas.

2. Apparatus for controlling the temperature of an oxygen sensor having an output upon which a DC output signal appears whose level is indicative of oxygen concentration and whose output impedance varies with temperature, comprising:
    oscillator means for providing an AC signal;
    means for applying said AC signal to said output of said sensor so that said AC signal appears across the output of said sensor superimposed on said DC output signal and has an amplitude dependent upon the impedance of said sensor, whereby the amplitude of said AC signal appearing at the output of said sensor indicates the output impedance of, and hence the temperature of, said sensor;
    separation means for separating said superimposed AC and DC signals,
    first means for utilizing said DC signal as an indication of said oxygen concentration; and
    second means for controlling the temperature of said sensor in accordance with the amplitude of said AC signal.

3. Apparatus as set forth in claim 2, wherein said means for applying comprises impedance means for providing a known electrical impedance in the AC signal path between said oscillator means and said output of said sensor, whereby the amplitude of said AC signal appearing at said output of said sensor is dependent upon the relative sizes of said known impedance and said output impedance of said sensor.

4. Apparatus as set forth in claim 3, wherein said impedance means has a higher impedance at the frequencies associated with said DC signal than at the frequencies associated with said AC signal whereby loading on said sensor output is reduced.

5. Apparatus as set forth in claim 2, wherein said separating means comprises a high-pass filter responsive to said superimposed signals for passing only said AC signal to said second means and a low-pass filter also responsive to said superimposed signals for passing only said DC signals to said first means.

6. Apparatus as set forth in claim 2, wherein said sensor comprises a zirconium dioxide oxygen sensor.

* * * * *